United States Patent [19]

Friday

[11] Plant 5,223

[45] Apr. 24, 1984

[54] PEACH TREE

[75] Inventor: James Friday, Coloma, Mich.

[73] Assignee: Hilltop Orchards & Nurseries, Inc., Hartford, Mich.

[21] Appl. No.: 333,122

[22] Filed: Dec. 21, 1981

[51] Int. Cl.[3] ..... A01H 5/03

[52] U.S. Cl. ..... Plt/43

[58] Field of Search ..... Plt./43

*Primary Examiner*—Robert E. Bagwill

*Attorney, Agent, or Firm*—John R. Nesbitt

[57] ABSTRACT

This invention relates to a new cultivar of peach tree which is highly colored, has uniform ripening, and is early bearing.

1 Drawing Figure

This invention is a new and distinct cultivar of peach tree. It was discovered in a cultivated area as a whole tree seedling by James Friday on his farm located at Rt. #1 Friday Road, Coloma Township, Berrien County, Mich. about August, 1963.

The tree aforesaid was planted for test purposes at an orchard of Hilltop Orchards & Nurseries, Inc., near Hartford, Mich., and was assigned the number JF-232. The tree has been asexually reproduced and remains true to type.

The present new cultivar, which applicant hereby assigns the varietal name of "Friday", has been assigned the Hilltop House brand name of the "Jim-Dandee" peach tree.

THE DRAWINGS

FIG. 1 is a color photograph showing a typical example of fruit, both top and bottom views, and in cross sections, and foliage of the Friday Peach.

DETAILED DESCRIPTION

The following is a detailed description of the new cultivar: (The color descriptions hereinafter mentioned are based on the Munsell Hue Color Chart).

Habit: Medium vigor, quite spreading, resembles Redhaven.

Disease: Bacterial spot susceptible, but no commercial problem.

Leaf: Dark green, medium to large, long and pointed with short leafstalk. Serrations are distinct, shallow, curved forward, medium in size and regular. Glands are near leafblade, reddish, somewhat oval with depressed centers. The leaf is Munsell hue green 4/2Y-GY.

Flower: Non-showy, similar to Redhaven with comparable flower bud hardiness.

Fruit

Size and shape: Large, about 2¾" in diameter, much larger than Redhaven, with a distinctive pointed end.

Color: When compared to Redhaven, the fruit has a much brighter red overcolor, with mottled appearance. The ground color is a bright yellow.

Pit size: Medium.

Flesh: The flesh is Munsell hue 7/2YR-Y. Yellow, with a red pit cavity which infiltrates into the flesh.

Skin: Smooth with little pubescence. The skin is Munsell hue as follows: (1) the yellowish undercolor or ground color is 5/2R-YR: and (2) the overcolor is reddish and rates 6/2YR-Y.

Texture: Firm, somewhat coarse, melting.

Quality: Good.

Aroma: Very pleasant.

Maturity: Midseason about eight days after Redhaven, with more uniform ripening.

Keeping quality: Excellent keeping and shipping qualities.

Use: As a commercial fresh market shipping peach.

I claim:

1. A new and distinct peach tree substantially as shown and described.

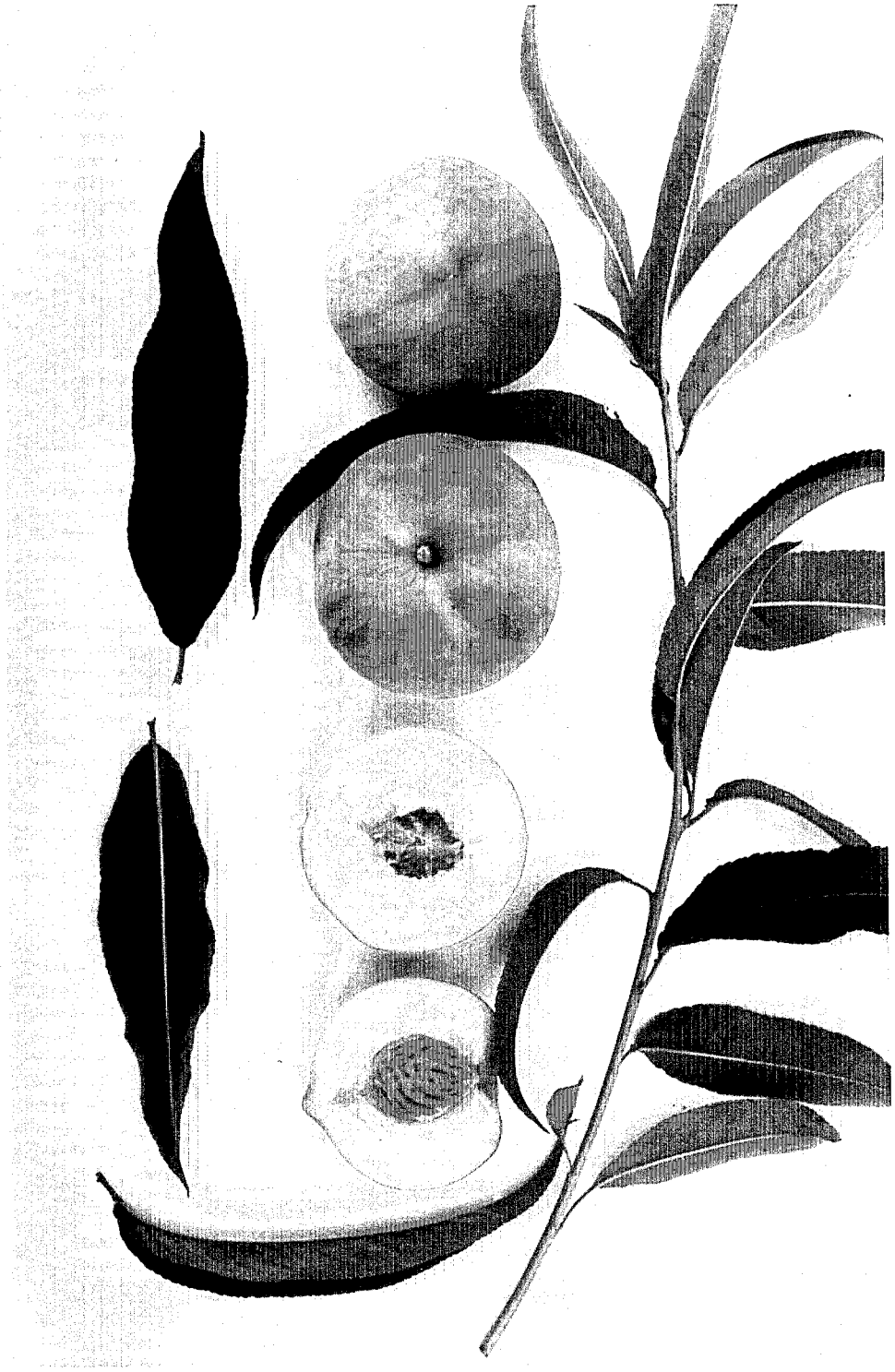

* * * * *